(12) United States Patent
LeBoeuf et al.

(10) Patent No.: US 8,647,270 B2
(45) Date of Patent: Feb. 11, 2014

(54) FORM-FITTED MONITORING APPARATUS FOR HEALTH AND ENVIRONMENTAL MONITORING

(75) Inventors: Steven Francis LeBoeuf, Raleigh, NC (US); Jesse Berkley Tucker, Knightdale, NC (US); Michael Edward Aumer, Raleigh, NC (US)

(73) Assignee: Valencell, Inc., Raleigh, NC (US)

( * ) Notice: Subject to any disclaimer, the term of this patent is extended or adjusted under 35 U.S.C. 154(b) by 611 days.

(21) Appl. No.: 12/692,807

(22) Filed: Jan. 25, 2010

(65) Prior Publication Data
US 2010/0217098 A1    Aug. 26, 2010

Related U.S. Application Data

(60) Provisional application No. 61/208,567, filed on Feb. 25, 2009, provisional application No. 61/208,574, filed on Feb. 25, 2009, provisional application No. 61/212,444, filed on Apr. 13, 2009, provisional application No. 61/274,191, filed on Aug. 14, 2009.

(51) Int. Cl.
*A61B 5/00* (2006.01)

(52) U.S. Cl.
USPC .......................................... 600/301; 600/300

(58) Field of Classification Search
USPC .......... 600/300, 301, 310–336; 128/903–905, 128/920
See application file for complete search history.

(56) References Cited

U.S. PATENT DOCUMENTS

| | | | | |
|---|---|---|---|---|
| 5,673,692 A | * | 10/1997 | Schulze et al. | 600/301 |
| 6,078,829 A | * | 6/2000 | Uchida et al. | 600/310 |
| 7,483,730 B2 | * | 1/2009 | Diab et al. | 600/344 |
| 8,055,319 B2 | * | 11/2011 | Oh et al. | 600/310 |
| 2004/0054291 A1 | | 3/2004 | Schulz et al. | |
| 2005/0148883 A1 | | 7/2005 | Boesen | |
| 2008/0132798 A1 | * | 6/2008 | Hong et al. | 600/508 |
| 2008/0146890 A1 | | 6/2008 | LeBoeuf et al. | |
| 2008/0154098 A1 | * | 6/2008 | Morris et al. | 600/300 |
| 2008/0200774 A1 | * | 8/2008 | Luo | 600/301 |
| 2009/0030350 A1 | | 1/2009 | Yang et al. | |
| 2009/0088611 A1 | * | 4/2009 | Buschmann | 600/301 |
| 2009/0131761 A1 | * | 5/2009 | Moroney, III et al. | 600/301 |
| 2010/0228315 A1 | * | 9/2010 | Nielsen | 607/42 |

OTHER PUBLICATIONS

Notification of Transmittal of the International Search Report and the Written Opinion of the Searching Authority issued Jul. 30, 2010 by the Korean Intellectual Property Office for corresponding international application No. PCT/US2010/021936.

\* cited by examiner

*Primary Examiner* — Bill Thomson
*Assistant Examiner* — Davin K Sands
(74) *Attorney, Agent, or Firm* — Myers Bigel Sibley & Sajovec, P.A.

(57) ABSTRACT

A monitoring apparatus includes a housing that is configured to be attached to a body of a subject. The housing includes a sensor region that is configured to contact a selected area of the body of the subject when the housing is attached to the body of the subject. The sensor region is contoured to matingly engage the selected body area. The apparatus includes at least one physiological sensor that is associated with the sensor region and that detects and/or measures physiological information from the subject and/or at least one environmental sensor associated with the sensor region that is configured to detect and/or measure environmental information. The sensor region contour stabilizes the physiological and/or environmental sensor(s) relative to the selected body area such that subject motion does not impact detection and/or measurement efforts of the sensor(s).

45 Claims, 8 Drawing Sheets

FORM-FITTED MONITORING APPARATUS FOR HEALTH AND ENVIRONMENTAL MONITORING

RELATED APPLICATIONS

This application claims the benefit of and priority to U.S. Provisional Patent Application No. 61/208,567 filed Feb. 25, 2009, U.S. Provisional Patent Application No. 61/208,574 filed Feb. 25, 2009, U.S. Provisional Patent Application No. 61/212,444 filed Apr. 13, 2009, and U.S. Provisional Patent Application No. 61/274,191 filed Aug. 14, 2009, the disclosures of which are incorporated herein by reference as if set forth in their entireties.

FIELD OF THE INVENTION

The present invention relates generally to health and environmental monitoring and, more particularly, to health and environmental monitoring apparatus.

BACKGROUND OF THE INVENTION

There is growing market demand for personal health and environmental monitors, for example, for gauging overall health and metabolism during exercise, athletic training, dieting, daily life activities, sickness, and physical therapy. However, traditional health monitors and environmental monitors may be bulky, rigid, and uncomfortable—generally not suitable for use during daily physical activity. There is also growing interest in generating and comparing health and environmental exposure statistics of the general public and particular demographic groups. For example, collective statistics may enable the healthcare industry and medical community to direct healthcare resources to where they are most highly valued. However, methods of collecting these statistics may be expensive and laborious, often utilizing human-based recording/analysis steps at multiple sites.

As such, improved ways of collecting, storing and analyzing physiological information are needed. In addition, improved ways of seamlessly extracting physiological information from a person during everyday life activities, especially during high activity levels, may be important for enhancing fitness training and healthcare quality, promoting and facilitating prevention, and reducing healthcare costs.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

According to some embodiments of the present invention, a monitoring apparatus includes a housing that is configured to be attached to a body of a subject, and that has a sensor region that is configured to contact a selected area of the body of the subject when the housing is attached to the body of the subject. The sensor region is contoured (i.e., is "form-fitted") to matingly engage the selected body area. The apparatus includes at least one physiological sensor that is associated with the sensor region and that detects and/or measures physiological information from the subject and/or at least one environmental sensor associated with the sensor region that is configured to detect and/or measure environmental information. The sensor region contour stabilizes the physiological and/or environmental sensor(s) relative to the selected body area such that subject motion does not negatively impact detection and/or measurement efforts of the sensor(s). In some embodiments, the sensor region contour stabilizes the housing of the monitoring apparatus when the housing is attached to the body of the subject. An exemplary monitoring apparatus, according to embodiments of the present invention is a headset having an earbud module and wherein the sensor region is a portion of the housing of the earbud module.

The sensor region of a monitoring apparatus, according to some embodiments of the present invention, can have various characteristics. For example, in some embodiments, at least a portion of the sensor region is detachable from the housing. In some embodiments, at least a portion of the sensor region is configured to block energy transferred between the subject and a physiological sensor. In some embodiments, at least a portion of the sensor region is configured to guide energy transferred between the subject and a physiological sensor. For example, the sensor region may include a lens that is configured to focus light transferred between the subject and a physiological sensor.

In some embodiments of the present invention, a monitoring apparatus housing may have a plurality of sensor regions, each configured to contact a respective selected area of the body of a subject when the housing is attached to the body of the subject. Each sensor region is contoured (i.e., "form-fitted") to matingly engage a respective selected body area. One or more physiological sensors may be associated with each sensor region and configured to detect and/or measure physiological information from the subject. In some embodiments, at least one sensor region of a monitoring apparatus has one or more sensors associated therewith that are configured to measure motion of the subject. Sensors for measuring motion may include, but are not limited to, sensors that measure changes in one or more of the following: inertia, capacitance, electrical conductivity, inductance, speed, distance, acceleration, and electromagnetic radiation.

In some embodiments, a sensor region of a monitoring apparatus may include a cover that is detachably secured to the sensor region. In some embodiments, the cover may be configured to regulate energy transferred between the subject and the physiological sensor. For example, the cover may be configured to block or filter certain types of energy.

According to some embodiments of the present invention, a monitoring apparatus includes a housing that is configured to be attached to a body of a subject, a physiological sensor supported by the housing and configured to detect and/or measure physiological information from the subject, and a plurality of interchangeable articles, each configured to be removably secured to the housing one at a time and each having a respective different shape. Each article is adapted to contact a selected body area when the housing is attached to the body of the subject, and the physiological sensor detects and/or measures physiological information from the subject via each article when removably secured to the housing. In some embodiments, each article is contoured to matingly engage the selected body area. The contour of each article may stabilize the housing when the housing is attached to the body of the subject. In some embodiments, each interchangeable article may include one or more physiological and/or environmental sensors.

According to some embodiments of the present invention, an earbud for a headset includes a housing that is configured to be positioned within an ear of a subject. The housing includes a sensor region that is configured to contact a selected area of the ear when the housing is attached to the ear of the subject. At least one physiological sensor is associated with the sensor region that detects and/or measures physiological information from the subject and/or at least one environmental sensor is associated with the sensor region and is configured to detect and/or measure environmental information. The sensor region is contoured to matingly engage the selected ear area and to stabilize the physiological and/or environmental sensor(s) relative to the selected ear area. In some embodiments, the sensor region contour stabilizes the housing when the housing is attached to the ear of the subject.

The sensor region of a monitoring apparatus, according to some embodiments of the present invention, can have various characteristics. For example, in some embodiments, at least a portion of a sensor region is detachable from the housing of the apparatus. In some embodiments, at least a portion of a sensor region is configured to block energy transferred between the subject and a physiological sensor. In some embodiments, at least a portion of a sensor region is configured to guide energy transferred between the subject and a physiological sensor. For example, a sensor region may include a lens that is configured to focus light transferred between the subject and a physiological sensor.

In some embodiments of the present invention, an earbud housing may have a plurality of sensor regions, each configured to contact a respective selected area of the ear of a subject when the housing is attached to the ear of the subject. Each sensor region is contoured (i.e., "form-fitted") to matingly engage a respective selected ear area. One or more physiological sensors may be associated with each sensor region and configured to detect and/or measure physiological information from the subject. In some embodiments, at least one sensor region of an earbud has one or more sensors associated therewith that are configured to measure motion of the subject. Sensors for measuring motion may include, but are not limited to, sensors that measure changes in one or more of the following: inertia, capacitance, electrical conductivity, inductance, speed, distance, acceleration, and electromagnetic radiation.

In some embodiments, a sensor region of an earbud may include a cover that is detachably secured to the sensor region. In some embodiments, the cover may be configured to regulate energy transferred between a subject and the physiological sensor. For example, the cover may be configured to block or filter certain types of energy.

Monitoring apparatus, according to the various embodiments of the present invention, may be utilized with mono headsets (i.e., headsets having one earbud) as well as stereo headsets (i.e., headsets having two earbuds). Moreover, earbuds according to the various embodiments of the present invention may be utilized with hearing aids, body jewelry, or any other attachment that can be placed near the head region, such as eye glasses or shades, a headband, a cap, helmet, face mask, visor, or the like.

BRIEF DESCRIPTION OF THE DRAWINGS

The accompanying drawings, which form a part of the specification, illustrate various embodiments of the present invention. The drawings and description together serve to fully explain embodiments of the present invention.

DETAILED DESCRIPTION

Figure 1:
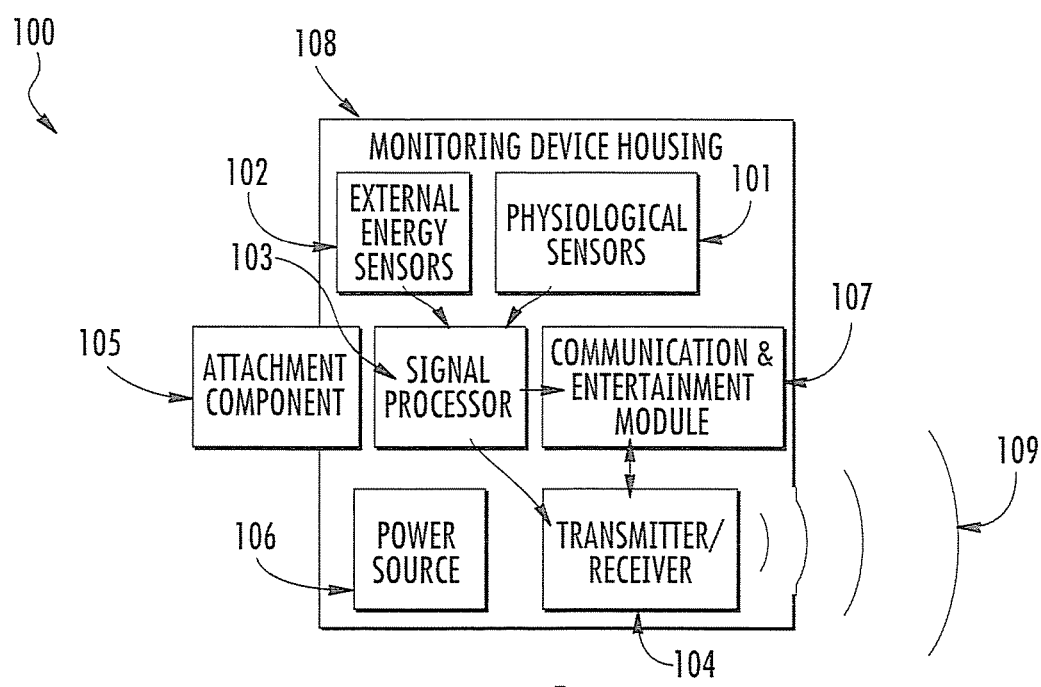
FIG. 1 is a block diagram of a monitoring device for physiological and environmental monitoring, according to some embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. Features described with respect to one figure or embodiment can be associated with another embodiment or figure although not specifically described or shown as such.

It will be understood that when a feature or element is referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that although the terms first and second are used herein to describe various features/elements, these features/elements should not be limited by these terms. These terms are only used to distinguish one feature/element from another feature/element. Thus, a first feature/element discussed below could be termed a second feature/element, and similarly, a second feature/element discussed below could be termed a first feature/element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "headset" includes any type of device or earpiece that may be attached to or near the ear (or ears) of a user and may have various configurations, without limitation. Headsets incorporating "form-fitted" sensor regions, as described herein, may include mono headsets (one earbud) and stereo headsets (two earbuds).

The term "real-time" is used to describe a process of sensing, processing, or transmitting information in a time frame which is equal to or shorter than the minimum timescale at which the information is needed. For example, the real-time monitoring of pulse rate may result in a single average pulse-rate measurement every minute, averaged over 30 seconds, because an instantaneous pulse rate is often useless to the end user. Typically, averaged physiological and environmental information is more relevant than instantaneous changes. Thus, in the context of the present invention, signals may sometimes be processed over several seconds, or even minutes, in order to generate a "real-time" response.

The term "monitoring" refers to the act of measuring, quantifying, qualifying, estimating, sensing, calculating, interpolating, extrapolating, inferring, deducing, or any combination of these actions. More generally, "monitoring" refers to a way of getting information via one or more sensing elements. For example, "blood health monitoring" includes monitoring blood gas levels, blood hydration, and metabolite/electrolyte levels.

The term "physiological" refers to matter or energy of or from the body of a subject (e.g., humans, animals, etc.). In embodiments of the present invention, the term "physiological" is intended to be used broadly, covering both physical and psychological matter and energy of or from the body of a creature. However, in some cases, the term "psychological" is called-out separately to emphasize aspects of physiology that are more closely tied to conscious or subconscious brain activity rather than the activity of other organs, tissues, or cells.

The term "body" refers to the body of a subject (human or animal) that may wear a form-fitted monitoring apparatus, according to embodiments of the present invention.

According to some embodiments of the present invention, monitoring apparatus containing one or more physiological and/or environmental monitors or sensors that have a shape or configuration that is form-fitted to a portion of the body of a subject are provided. The term "form-fitted" means that a monitoring apparatus, or one or more portions thereof, has a specific shape or configuration for mating engagement with a specific portion of the anatomy of a subject. This mating engagement provides stability that enhances monitoring efforts by the sensors associated therewith.

The ear is an ideal location for wearable health and environmental monitors. The ear is a relatively immobile platform that does not obstruct a person's movement or vision. Headsets located at an ear have, for example, access to the inner-ear canal and tympanic membrane (for measuring core body temperature), muscle tissue (for monitoring muscle tension), the pinna and earlobe (for monitoring blood gas levels), the region behind the ear (for measuring skin temperature and galvanic skin response), and the internal carotid artery (for measuring cardiopulmonary functioning), etc. The ear is also at or near the point of exposure to: environmental breathable toxicants of interest (volatile organic compounds, pollution, etc.); noise pollution experienced by the ear; and lighting conditions for the eye. Furthermore, as the ear canal is naturally designed for transmitting acoustical energy, the ear provides a good location for monitoring internal sounds, such as heartbeat, breathing rate, and mouth motion.

According to some embodiments of the present invention, monitoring apparatus with form-fitted portions for attachment to or near the ear of a subject include various types of headsets, including wired or wireless headsets. Bluetooth®-enabled and/or other personal communication headsets may be configured to incorporate physiological and/or environmental sensors, according to some embodiments of the present invention. Bluetooth® headsets are typically lightweight, unobtrusive devices that have become widely accepted socially. Moreover, Bluetooth® headsets may be cost effective, easy to use, and are often worn by users for most of their waking hours while attending or waiting for cell phone calls. Bluetooth® headsets configured according to embodiments of the present invention are advantageous because they provide a function for the user beyond health monitoring, such as personal communication and multimedia applications, thereby encouraging user compliance with monitoring. Exemplary physiological and environmental sensors that may be incorporated into a Bluetooth® or other type of headsets include, but are not limited to accelerometers, acoustic sensors, auscultatory sensors, pressure sensors, humidity sensors, color sensors, light intensity sensors, pressure sensors, etc.

Headsets, both mono (single earbud) and stereo (dual earbuds), incorporating low-profile sensors and other electronics, according to embodiments of the present invention, offer a platform for performing near-real-time personal health and environmental monitoring in wearable, socially acceptable devices. The capability to unobtrusively monitor an individual's physiology and/or environment, combined with improved user compliance, is expected to have significant impact on future planned health and environmental exposure studies. This is especially true for those that seek to link environmental stressors with personal stress level indicators. The large scale commercial availability of a low-cost headset device can enable cost-effective large scale studies. The combination of monitored data with user location via GPS data can make on-going geographic studies possible, including the tracking of infection over large geographic areas. The commercial application of the proposed platform encourages individual-driven health maintenance and promotes a healthier lifestyle through proper caloric intake and exercise.

Accordingly, some embodiments of the present invention combine a personal communications headset device with one or more physiological and/or environmental sensors. Embodiments of the present invention are not limited to headsets that communicate wirelessly. In some embodiments of the present invention, headsets configured to monitor an individual's physiology and/or environment may be wired to a device that stores and/or processes data. In some embodiments, this information may be stored on the headset itself.

Although some embodiments illustrated herein are devices, such as headsets, that are configured to be attached at or near the ear of a subject, it is understood that form-fitted monitoring apparatus according to embodiments of the present invention can be utilized in proximity to any portion of the body of a subject, such as the limbs, torso, head, etc. In the case of an apparatus configured to sense physiological and/or environmental information near the ear region of a subject, any part of such an earpiece/headset device may have a form-fitted configuration.

FIG. 1 is a block diagram illustrating an earpiece module 100 that may include a form-fitted portion for attachment at or near the ear of a subject, according to some embodiments of the present invention. The illustrated earpiece module 100 includes one or more of the following: at least one physiological sensor 101, at least one environmental sensor 102 (also referred to as an external energy sensor), at least one signal processor 103, at least one transmitter/receiver 104, at least one power source 106, at least one communication & entertainment module 107, at least one earpiece attachment component 105, and at least one housing 108. Though the health and environmental sensor functionality can be obtained without the communication and entertainment module 107, having this additional module may promote use of the earpiece module 100 by users. The illustrated earpiece module 100 is intended primarily for human use; however, the earpiece module 100 may also be configured for use with other animals having ears sufficient to support an earpiece, such as primates, canines, felines, cattle, and most other mammals.

Earpiece monitoring apparatus according to embodiments of the present invention are not limited to the illustrated configuration of FIG. 1. A monitoring apparatus according to embodiments of the present invention may have only one or more physiological sensors, only one or more environmental sensors, or a combination of one or more physiological and environmental sensors. In some embodiments, a monitoring apparatus may not have one or more of the following: an earpiece attachment component 105, a communication and entertainment module 107, a signal processor 103, or a transmitter/receiver 104.

A physiological sensor 101 can be any compact sensor for monitoring the physiological functioning of the body, such as, but not limited to, sensors for monitoring: heart rate, pulse rate, breathing rate, blood flow, $VO_2$, $VO_{2max}$, blood oxygen, blood constituent levels, blood glucose level, heartbeat signatures, cardio-pulmonary health, organ health, metabolism, electrolyte type and concentration, physical activity, caloric intake, caloric metabolism, metabolomics, physical and psychological stress levels and stress level indicators, physiological and psychological response to therapy, drug dosage and activity (drug dosimetry), physiological drug reactions, drug chemistry in the body, biochemistry, position & balance, body strain, neurological functioning, brain activity, brain waves, blood pressure, cranial pressure, hydration level, auscultatory information, auscultatory signals associated with pregnancy, physiological response to infection, skin and core body temperature, eye muscle movement, blood volume, inhaled and exhaled breath volume, physical exertion, exhaled breath physical and chemical composition, the presence, identity, and concentration of viruses & bacteria, foreign matter in the body, internal toxins, heavy metals in the body, anxiety, fertility, ovulation, sex hormones, psychological mood, sleep patterns, hunger & thirst, hormone type and concentration, cholesterol, lipids, blood panel, bone density, body fat density, muscle density, organ and body weight, reflex response, sexual arousal, mental and physical alertness, sleepiness, auscultatory information, response to external stimuli, swallowing volume, swallowing rate, sickness, voice characteristics, tone, pitch, and volume of the voice, vital signs, head tilt, allergic reactions, inflammation response, auto-immune response, mutagenic response, DNA, proteins, protein or lactate levels in the blood, body hydration, water content of the blood, pheromones, internal body sounds, digestive system functioning, cellular regeneration response, healing response, stem cell regeneration response, and the like. Vital signs can include pulse rate, breathing rate, blood pressure, pulse signature, body temperature, hydration level, skin temperature, and the like. A physiological sensor may include an impedance plethysmograph for measuring changes in volume within an organ or body (usually resulting from fluctuations in the amount of blood or air it contains). For example, the earpiece module 100 may include an impedance plethysmograph to monitor blood pressure in real-time.

An external energy sensor 102, serving primarily as an environmental sensor, can be any compact sensor for monitoring the external environment in the vicinity of the body, such as, but not limited to, sensors for monitoring: climate, humidity, temperature, pressure, barometric pressure, pollution, automobile exhaust, soot density, airborne particle density, airborne particle size, airborne particle shape, airborne particle identity, volatile organic chemicals (VOCs), hydrocarbons, polycyclic aromatic hydrocarbons (PAHs), carcinogens, toxins, electromagnetic energy (optical radiation, X-rays, gamma rays, microwave radiation, terahertz radiation, ultraviolet radiation, infrared radiation, radio waves, and the like), EMF energy, atomic energy (alpha particles, beta-particles, gamma rays, and the like), gravity, light properties (such as intensity, frequency, flicker, and phase), ozone, carbon monoxide, greenhouse gases, $CO_2$, nitrous oxide, sulfides, airborne pollution, foreign material in the air, biological particles (viruses, bacteria, and toxins), signatures from chemical weapons, wind, air turbulence, sound and acoustical energy (both human audible and inaudible), ultrasonic energy, noise pollution, human voices, animal sounds, diseases expelled from others, the exhaled breath and breath constituents of others, toxins from others, bacteria & viruses from others, pheromones from others, industrial and transportation sounds, allergens, animal hair, pollen, exhaust from engines, vapors & fumes, fuel, signatures for mineral deposits or oil deposits, snow, rain, thermal energy, hot surfaces, hot gases, solar energy, hail, ice, vibrations, traffic, the number of people in a vicinity of the user, the number of people encountered throughout the day, other earpiece module users in the vicinity of the earpiece module user, coughing and sneezing sounds from people in the vicinity of the user, loudness and pitch from those speaking in the vicinity of the user, and the like.

Because the illustrated earpiece module 100 is capable of measuring and transmitting sensor information in real-time over a duration of time, the physiological and environmental sensors 101, 102 can be used to sense the aforementioned parameters over time, enabling a time-dependent analysis of the user's health and environment as well as enabling a comparison between the user's health and environment. Combined with proximity or location detection, this allows an analysis for pinpointing the location where environmental stress and physical strain took place. The signal processor 103 provides a means of converting the digital or analog signals from the sensors 101, 102 into data that can be transmitted wirelessly by the transmitter 104. The signal processor 103 may be composed of, for example, signal conditioners, amplifiers, filters, digital-to-analog and analog-to-digital converters, digital encoders, modulators, mixers, multiplexers, transistors, various switches, microprocessors, or the like. For personal communication, the signal processor 103 processes signals received by the receiver 104 into signals that can be heard or viewed by the user. The received signals may also contain protocol information for linking various telemetric modules together, and this protocol information can also be processed by the signal processor 103. The signal processor 103 may utilize one or more "compression/decompression" algorithms used in digital media (CODECs) for processing data. The transmitter/receiver 104 can be comprised of a variety of compact electromagnetic transmitters. A standard compact antenna is used in the standard Bluetooth headset protocol, but any kind of electromagnetic antenna suitable for transmitting at human-safe electromagnetic frequencies may be utilized. The transmitter/receiver 104 can also be an antenna. In some embodiments, the receiving antenna and the transmitting antenna are physically the same. The receiver/transmitter 104 can be, for example, a non-line-of-sight (N LOS) optical scatter transmission system. These systems typically use short-wave (blue or UV) optical radiation or "solar blind" (deep-UV) radiation in order to promote optical scatter, but IR wavelengths can also suffice. Additionally, a sonic or ultrasonic transmitter can be used as the receiver/transmitter 104 of the earpiece module 100, but preferably using sounds that are higher or lower than the human hearing range. A variety of sonic and ultrasonic receivers and transmitters are available in the marketplace and may be utilized in accordance with embodiments of the present invention.

In some embodiments, the transmitter/receiver 104 is configured to transmit signals from a signal processor 103 to a remote terminal following a predetermined time interval. For example, the transmitter/receiver 104 may delay transmission until a certain amount of detection time has elapsed, until a certain amount of processing time has elapsed, etc.

The power source 106 can be any portable power source capable of fitting inside the earpiece module housing 108. According to some embodiments, the power source 106 is a portable rechargeable lithium-polymer or zinc-air battery. Additionally, portable energy-harvesting power sources can be integrated into the earpiece module 100 and can serve as a primary or secondary power source. For example, a solar cell module can be integrated into the earpiece module 100 for collecting and storing solar energy. Additionally, piezoelectric devices or microelectromechanical systems (MEMS) can be used to collect and store energy from body movements, electromagnetic energy, and other forms of energy in the environment or from the user himself. A thermoelectric or thermovoltaic device can be used to supply some degree of power from thermal energy or temperature gradients. In some embodiments, a cranking or winding mechanism can be used to store mechanical energy for electrical conversion or to convert mechanical energy into electrical energy that can be used immediately or stored for later.

The various components describe above are configured to fit within the earpiece housing 108 and/or be attached thereto. The earpiece housing 108 may be formed from any safe and comfortable solid material, such as metal, rubber, wood, polymers, ceramic, organic materials, or various forms of plastic. The earpiece attachment component 105 is attached to the earpiece housing 108 and is designed to fit around or near the ear. For example, the standard Bluetooth headset includes an earpiece attachment that is connected to the headset housing via a double-jointed socket, to provide comfort and positioning flexibility for the user. In some embodiments, the earpiece attachment component 105 can be part of the housing 108, such that the entire earpiece module is one largely inflexible, rigid unit. In such case, a counterweight may be incorporated into the earpiece module 100 to balance the weight of the earpiece electronics and power source. In some embodiments, the earpiece attachment component 105 can contain physiological and environmental sensors, and the earpiece attachment component 105 may be detachable. In some embodiments, more than one earpiece attachment 105 can be attached to the earpiece module housing 108.

Figure 2:
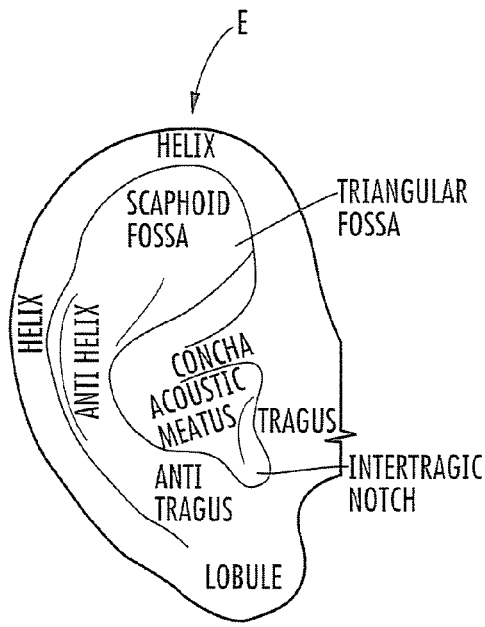
FIG. 2 illustrates the anatomy of a human ear.

FIG. 2 illustrates relevant anatomy of a human ear E. The anti tragus region is a particularly motion insensitive region for measuring physiological information from the ear during normal life activities. In contrast, a number of ear regions are particularly motion sensitive. For example, the ear canal, tragus, concha, helix, triangular fossa, intertragic notch, and neighboring regions may be particularly motion sensitive regions, especially when a person speaks, jogs, runs, etc. Placing sensors at these regions can be useful for generating signals that are entirely or mostly associated with motion only, with little (if any) signals associated with physiological information, or with contributions from both motion and physiological information. These signals can then be combined to generate a signal more closely associated with physiological information.

Figure 3:
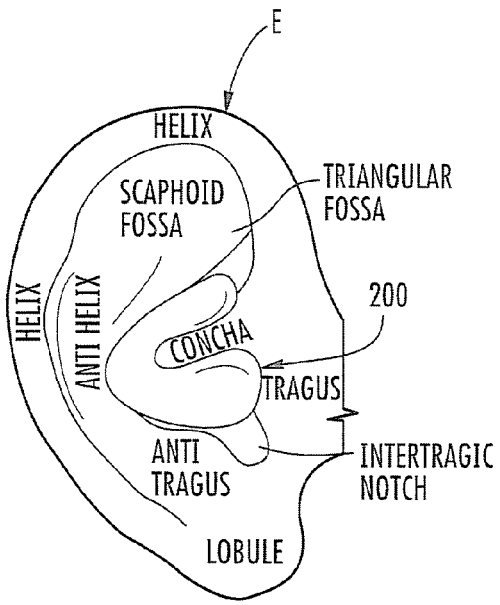
FIG. 3 illustrates a human ear with an earbud module attached thereto, according to some embodiments of the present invention.

FIG. 3 illustrates a monitoring apparatus 200, according to some embodiments of the present invention, attached to a human ear E. The monitoring apparatus 200 is an earbud module and is illustrated and described in more detail with respect to FIGS. 4A-4D.

Figure 4A:
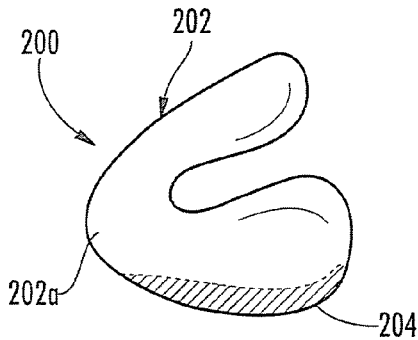
FIG. 4A is a front plan view of the earbud module of FIG. 3.
Figure 4B:
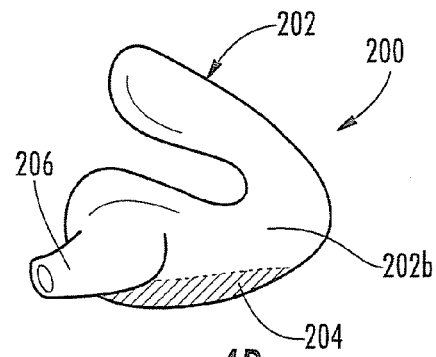
FIG. 4B is a rear plan view of the earbud module of FIG. 4A.
Figure 4C:
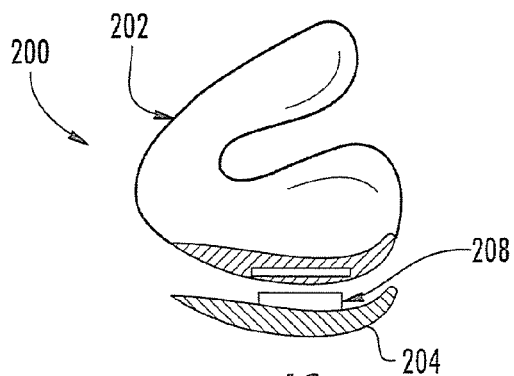
FIG. 4C is an exploded view of the earbud module of FIG. 4A with a detachable sensor region detached from the earbud housing, according to some embodiments of the present invention.

The illustrated monitoring apparatus 200 of FIG. 4A includes a housing 202 that is configured to be attached to the ear E of a subject, and that has a sensor region 204 that is configured to contact a selected area of the ear E when the housing 202 is attached to the ear E. The sensor region 204 is contoured (i.e., is "form-fitted") to matingly engage a portion of the ear E between the anti tragus and acoustic meatus. As known to those skilled in the art, the region of the ear E between the anti tragus and the acoustic meatus contains a network of blood vessels that contain physiological information. Applicants have unexpectedly discovered that the this region of the ear E is resistant to motion artifacts. The housing 202 has a front or outer surface 202*a* and a rear or inner surface 202*b*. An elongated, hollow tube 206 extends outwardly from the housing rear surface 202*b*, as illustrated, and is configured to be inserted within the ear canal of an ear E.

In the illustrated embodiment, the sensor region 204 may be removable and may be replaced with a sensor region having a different contour. In other embodiments, the sensor region may be a fixed portion of the apparatus 200. Because the shape of the region of an ear E between the anti tragus and the acoustic meatus may vary from subject to subject, a sensor region 204 can be selected that has a contour that best aligns with the contour of any given subject's ear. The illustrated sensor region 204 is removably secured to the housing 202 via a connector 208 (FIG. 4C) which is configured to allow ready removal and attachment from/to the housing 202. Various types of connectors may be utilized without limitation, and embodiments of the present invention are not limited to any particular type of connector.

Figure 4D:
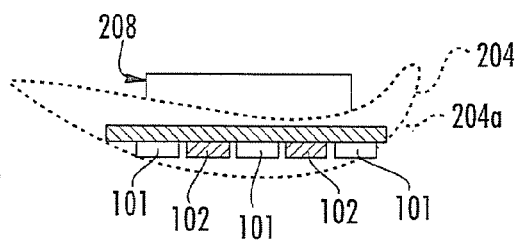
FIG. 4D is an enlarged plan view of the detachable sensor region of FIG. 4C.

As illustrated in FIG. 4D, the removable sensor region 204 contains physiological sensors 101 and environmental sensors 102, as described above. The physiological sensors 101 detect and/or measure physiological information from the subject and the environmental sensors 102 detect and/or measure environmental information, such as the ambient environment surrounding the person, environmental exposures by the person, environmental energy reaching the person, or the like. However, embodiments of the present invention are not limited to the illustrated removable sensor region with three physiological sensors 101 and two environmental sensors 102. As described above, one or more physiological sensors and/or one or more environmental sensors may be utilized. In some embodiments, one or more of the sensors 101, 102 may be configured to measure motion of a subject. Sensors for measuring motion may include, but are not limited to, sensors that measure changes in one or more of the following: inertia, capacitance, electrical conductivity, inductance, speed, distance, acceleration, and electromagnetic radiation.

In the illustrated embodiment, the sensors 101, 102 are embedded within the sensor region 204. The connector 208 may provide electrical contact between the sensors 101, 102 and another component(s) within the housing 202, such as a processor (103, FIG. 1), transmitter/receiver (104, FIG. 1), etc. In other embodiments, one or more of the sensors 101, 102 may be positioned on the surface 204*a* of the sensor region 204, or may be located at another region of the housing 202 in proximity to the sensor region 204.

Sensors 101, 102 utilized in or relative to sensor regions 204, according to embodiments of the present invention, are not limited to being in a planar configuration relative to each other. Sensors 101, 102 may be arranged in virtually any configuration on, within, and/or relative to a sensor region 204. In some embodiments two or more sensors 101, 102 may be arranged at angles to each other. In some embodiments, one or more sensors 101, 102 may be exposed via one or more openings or apertures in a sensor region 204. As a specific example, having an optical emitter and optical detector at an angle from each other (such as a 45 degree angle) may be helpful in reducing unwanted optical scatter from being detected by the optical detector. In this way, the optical energy reaching the optical detector may contain a greater ratio of physiological information with respect to optical scatter.

The sensor region contour stabilizes the physiological and/or environmental sensor(s) 101, 102 relative to the ear E such that subject motion does not negatively impact detection and/or measurement efforts of the sensor(s) 101, 102. In addition, the contour of the illustrated sensor region 204 stabilizes the housing 202 of the monitoring apparatus 200 when the housing 202 is attached to the ear E of a subject.

The sensor region 204 can have various characteristics. For example, in some embodiments, at least a portion of the sensor region 204 may be configured to block energy transferred between the subject and a physiological sensor 101. In some embodiments, at least a portion of the sensor region 204 may be configured to guide energy transferred between the subject and a physiological sensor 101. For example, the sensor region 204 may include a lens that is configured to focus light transferred between the subject and a physiological sensor. In some embodiments, the sensor region 204 may include a cover (not shown) that is detachably secured to the sensor region 204. The cover may be configured to regulate energy transferred between the subject and a sensor 101, 102 via the sensor region 204. For example, the cover may be configured to block or filter certain types of energy. In some embodiments, the sensor region 204 may be configured to modulate energy transferred between a blocked region and one or more sensors. As a specific example, the sensor region 204 may contain a material or structure that moves in response to physical motion, thereby modulating energy between a blocked region and a sensor.

Figure 7A:
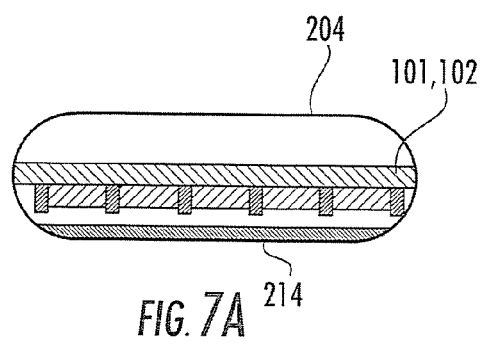
FIGS. 7A-7B are plan views of a sensor region for a monitoring apparatus, such as the earbud module of FIG. 6, according to some embodiments of the present invention.
Figure 7B:
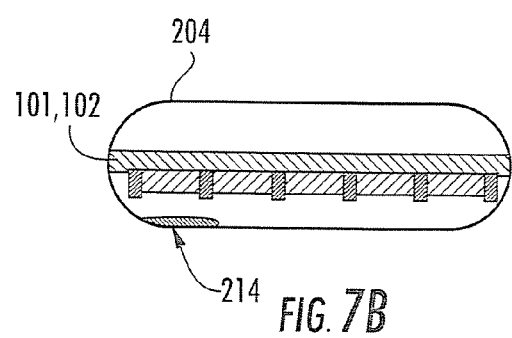
Figure 8A:
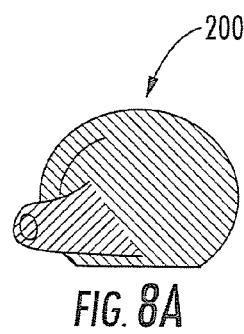
FIG. 8A is a front plan view of an earbud module, according to some embodiments of the present invention.
Figure 8B:
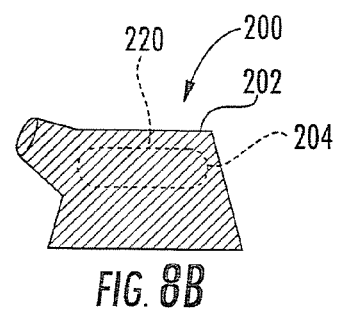
FIG. 8B is a bottom plan view of the earbud module of FIG. 8A.
Figure 8C:
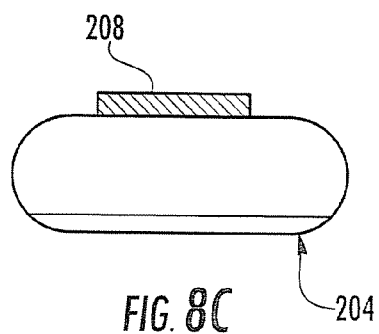
FIG. 8C is a front plan view of a detachable sensor region configured to be removably secured to the earbud module of FIG. 8A.
Figure 8D:
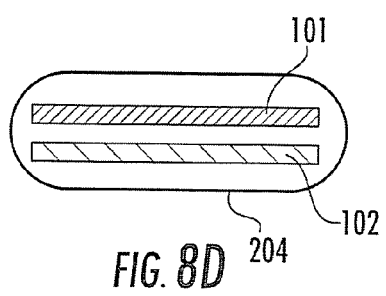
FIG. 8D is a bottom plan view of the detachable sensor region of FIG. 8C.

Referring now to FIGS. 7A-7B, a sensor region 204 for a monitoring apparatus 200, according to some embodiments of the present invention, is illustrated. The sensor region 204 may be a detachable sensor region as illustrated in FIGS. 4A-4D. The sensor region 204 may also be a non detachable portion of the housing of a monitoring device. The illustrated sensor region 204 includes at least one sensor (e.g., physiological sensor 101, environmental sensor 102) such as an optical sensor, embedded therewithin. The illustrated sensor region 204 also includes at least one energy regulating region 214 that is configured to manipulate optical energy moving to and/or from a physiological region of interest. Examples of energy manipulation include, but or not limited to, blocking, guiding, concentrating, accelerating/decelerating, diffusing, focusing, frequency-converting, scattering, filtering, and reflecting the energy. In some embodiments, the energy regulating region 214 may be applied to all or a portion of a sensor 101, 102 (or to a portion of the sensor region 204). For example, as illustrated in FIG. 7A, the energy regulating region 214 blocks light entirely from the optical sensor 101, 102. In this embodiment, the structure of FIG. 7A may serve as a noise sensor (noise source) for sensing body motion. This structure may be located at several regions along the earbud or along other parts of the body to sense motion and provide motion noise information that can be subtracted from other physiological sensors to provide a signal that is at least partially removed of motion artifacts. In other embodiments, as illustrated in FIG. 7B, a portion of the optical sensor 101, 102 is blocked by the energy regulating region 214 such that the light cannot reach a physiological region of interest. In this way, light may pass from at least one optical emitting element of the sensor 101 to the energy regulating region 214 and scatter to be detected by at least one optical detecting element of the sensor 101, 102. In some embodiments where the sensor region 204 is not rigid, this scattered light can be indicative of motion artifacts. This scattered light can be compared with light scattering from a physiological region to extract the physiological signal from unwanted motion artifacts. Similarly, the scattered light from the energy regulating region 214 can provide information on motion without corruption from physiological information.

In another embodiment, the energy regulating region 214 may filter light of one or more particular wavelength ranges, such that only certain wavelengths reach the skin. For example, if the energy regulating region incorporates an optical filter for passing only IR light to reach the skin, visible wavelengths emitted by one or more optical emitters will not reach the skin. In this way, visible wavelengths may be scattered and this scattering intensity may be indicative of physical motion. In contrast, the IR light scattering from the skin may have its intensity modulated by both physiological changes and motion-related changes. Thus, visible scattered light can be compared with IR light scattering from a physiological region to extract the physiological signal from unwanted motion artifacts. Similarly, the scattered light from the energy regulating region 214 can provide information on motion without corruption from physiological information.

Sensor 101, 102 in FIGS. 7A-7B need not be an optical sensor and the energy regulating region 214 need not be optical in nature. For example, sensor 101, 102 may be a capacitive sensor that can measure changes in electric field, where the electric field is selectively blocked by the energy regulating region 214 of sufficiently dissimilar permittivity or electrical conductivity region. Similarly, sensor 101, 102 may be an acoustic sensor that can measure changes in sound, where the sonic energy is selectively blocked by the energy regulating region 214 of dissimilar density. Similarly, the sensor 101, 102 may be a electrical conductivity sensor or electrode that can measure changes in electrical conductivity, where the electrical conductivity through the skin or body is selectively blocked by the energy regulating region 214 via an electrically insulating region. Similarly, the regulating region 214 may cover at least one emitter, detector, or combination of both. Similarly, sensor 101, 102 may be an optical sensor, and the energy regulating region 214 may include at least one mechanical structure, such as a flap, lever, membrane, or the like, for vibrating with physical motion. This vibration would modulate the optical energy in proportion to body motion. In some embodiments, the elements of FIGS. 7A-7B may be integrated into a microelectromechanical system (MEMS) device. In each case, changes in energy scatter from the energy regulating region 214 are predominantly associated with motion artifacts, whereas changes in energy scatter from the unregulated regions contains information on both physiological status and motion.

Monitoring apparatus and components thereof, according to embodiments of the present invention, can be fabricated by standard manufacturing techniques, including, but not limited to, injection molding, forming, extrusion, coating, and the like. In some embodiments, a sensor region 204 may be molded over sensor elements 101, 102 to yield a tight fit between these components. For optical sensors, the material composing the sensor region 204 is at least partially transparent to the relevant optical wavelengths. An energy regulating region 214 may be coated onto the surface 204a of a sensor region 204, incorporated into the material of the sensor region 204, or selectively deposited onto portions of the sensor region 204 or components thereof. Dielectric coatings and films may be utilized as coated energy regulating regions. For example, polyethylene film may be used to block UV light, and organic films and materials may be used to selectively pass light. For example, the materials in developed photographic film and certain dyes may pass IR light and reject other wavelengths. Similarly, Bragg reflector regions may be used to pass or reject certain wavelengths. In some embodiments, an energy regulating region 214 may be the same material as a sensor region 204. For example, optical-pass materials, such visible-pass, IR-pass plastics and UV-block plastics (such as polyethylene), may be suitable for regulating optical energy and may constitute at least part of the material used in a sensor region 204. In some embodiments, the material of a sensor region 204 may be doped and/or selectively doped with another material for regulating energy flow. Plastics and rubber as base materials may be ideal due to the soft, comfortable feel against the skin and the ability to form-fit these materials under compression.

Figure 11A:
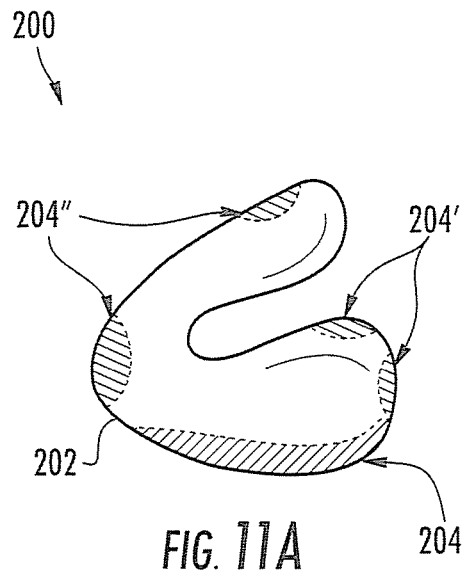
FIG. 11A is a rear plan view of an earbud module, according to some embodiments of the present invention.
Figure 11B:
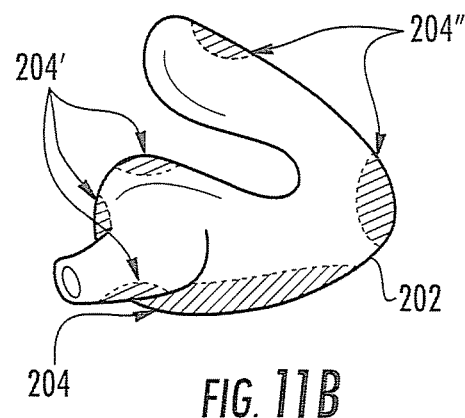
FIG. 11B is a front plan view of the earbud module of FIG. 11A.

In some embodiments of the present invention, a monitoring apparatus housing may have a plurality of sensor regions, each configured to contact a respective selected area of the body of the subject when the housing is attached to the body of the subject. Each sensor region may be contoured (i.e., "form-fitted") to matingly engage a respective selected body area. One or more physiological sensors 101 may be associated with each respective sensor region and configured to detect and/or measure physiological information from the subject. For example, as illustrated in FIGS. 11A-11B, the monitoring apparatus 200 of FIG. 4A may have a plurality of sensor regions 204, each configured to contact a respective selected area of the ear E of a subject when the housing 202 is attached to the ear. Each sensor region is contoured (i.e., "form-fitted") to matingly engage a respective selected ear region.

Figure 5A:
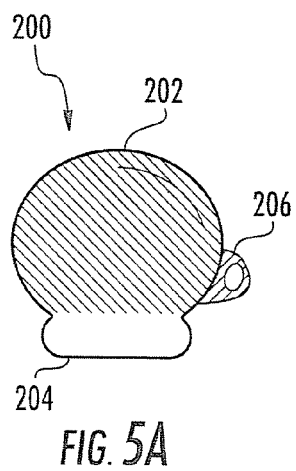
FIG. 5A is a rear plan view of an earbud module, according to some embodiments of the present invention.
Figure 5B:
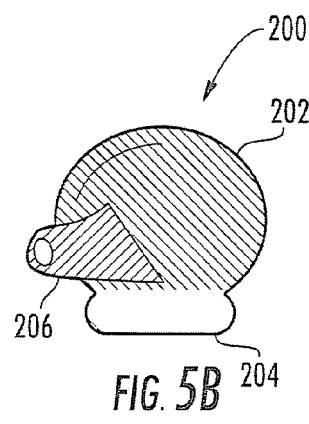
FIG. 5B is a front plan view of the earbud module of FIG. 5A.
Figure 5C:
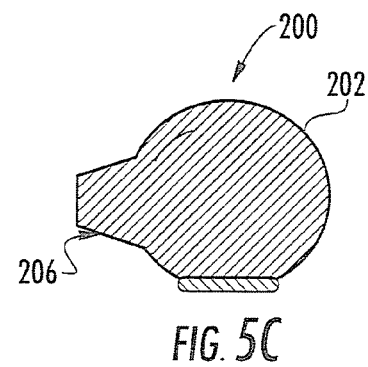
FIG. 5O is a front plan view of an earbud module, according to some embodiments of the present invention.

FIGS. 5A-5C illustrate a monitoring apparatus 200 in the form of an earbud module, according to other embodiments of the present invention. The illustrated apparatus 200 is essentially identical to the monitoring apparatus 200 of FIG. 4A except for the shape of the housing 202, which has a different configuration and which includes a sensor region 204 that is more bulbous than the sensor region 204 of FIG.

4A. The bulbous sensor region 204 is configured to fit snuggly between the anti tragus and acoustic meatus of a human ear. Because human ears have different shapes, different geometries of the sensor region 204 may be necessary for stabilizing the housing 202 within an ear E. For example, the sensor region 204 of FIG. 5C is smaller in size than the sensor region 204 depicted in FIG. 5B.

Figure 6:
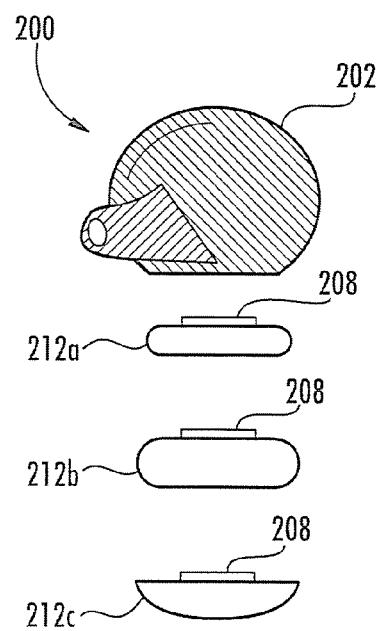
FIG. 6 is a an exploded view of an earbud module and a plurality of interchangeable articles configured to be removably secured to the earbud module, according to some embodiments of the present invention.

FIG. 6 illustrates a monitoring apparatus 200 according to some embodiments of the present invention having a housing 202 that is configured to be attached to the ear of a subject and that includes a plurality of interchangeable articles 212a-212c, each configured to be removably secured to the housing one at a time and each having a respective different shape. Each article 212a-212c is adapted to contact a selected ear area. One of the articles 212a-212c is selected depending on the shape of an ear in which the housing 202 is to be attached. For example, larger ears may require a larger article 212b, and curvier ears may require a curvier article 212c.

In some embodiments, these interchangeable articles 212a-212c may be sensor regions 204, as described above. In other embodiments, these interchangeable articles 212a-212c may be used only to provide stability to the housing 202 when attached to an ear. When used as sensor regions, each article 212a-212c may have various characteristics (e.g., block or filter certain types of energy, focus light, etc.) as described above. In addition, each article 212a-212c may include one or more physiological and/or environmental sensors.

Referring now to FIGS. 8A-8D, a monitoring apparatus 200, according to other embodiments of the present invention is illustrated. The illustrated monitoring apparatus 200 is an earbud module with a housing 202 having a portion 220 configured to removably receive a detachable sensor region 204 therein via connector 208. The sensor region 204 may contain one or more physiological sensors and/or one or more environmental sensors. In the illustrated embodiment, the sensor region 204 includes a physiological sensor 101 and an environmental sensor 102. These sensors may be spread out throughout the length of the sensor region 204 to provide a wider angle of sensor area such that motion artifacts have less of an impact on physiological sensing. In some embodiments, at least one sensor 101, 102 may be an optical sensor with a diffuse optical emitter. OLEDs and phosphor-coated LED sources are examples of diffuse optical emitters.

Figure 9A:
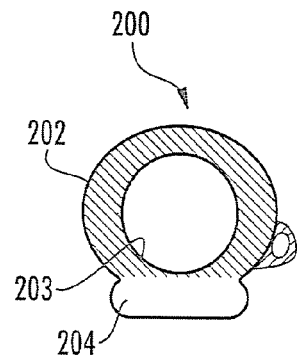
FIG. 9A is a rear plan view of an earbud module, according to some embodiments of the present invention.
Figure 9B:
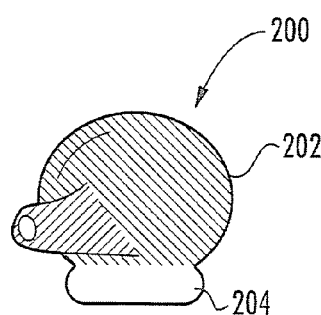
FIG. 9B is a front plan view of the earbud module of FIG. 9A.
Figure 9C:
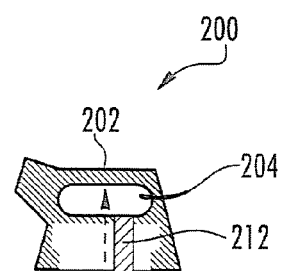
FIG. 9C is an exploded side view of the earbud module of FIG. 9A and a headset to which the earbud module is movably secured.

Referring to FIGS. 9A-9C, a monitoring apparatus 200, according to other embodiments of the present invention, is illustrated. The illustrated monitoring apparatus 200 is an earbud module with a housing 202 that is configured to be rotatably secured to a headset 300. The headset 300 includes a projecting portion 302 extending outwardly, as illustrated in FIG. 9C. This projecting portion 302 is configured to be inserted within a cavity 203 in the earpiece housing 202. This configuration allows the earbud module housing 202 and headset housing 300 to rotate relative to each other about axis $A_1$. Rotation may be needed to adjust the position of a microphone within the headset 300 relative to a mouth of a user. In the illustrated embodiment, an electrical connector 212 is shown and that extends from one or more sensors 101, 102 in the sensor region 204 through the projecting portion 302 for connecting the one or more sensors 101, 102 to a processor 103 or other component(s) in the headset housing 300.

The illustrated earbud module housing 202 includes a bulbous sensor region 204, similar to that described and illustrated in FIGS. 5A-5B. The bulbous sensor region 204 is configured to fit snuggly between the anti tragus and acoustic meatus of a human ear. The bulbous configuration of sensor region 204 allows the sensor region 204 to remain stable when the earbud module housing 202 and headset housing 300 rotate relative to each other about axis $A_1$. Stabilization provided by the sensor region 204 may be important because the swivel action may otherwise impart motion artifacts upon sensor(s) 101, 102 in the sensor region 204.

Figure 10A:
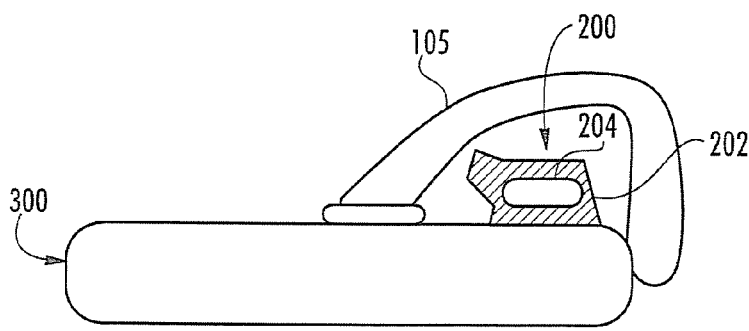
FIG. 10A is a side view of a headset and earbud module, according to some embodiments of the present invention.
Figure 10B:
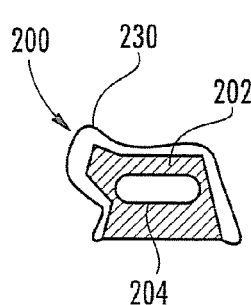
FIG. 10B is cross-sectional view of an earbud module for the headset of FIG. 10A with a cover, according to some embodiments of the present invention.
Figure 10C:
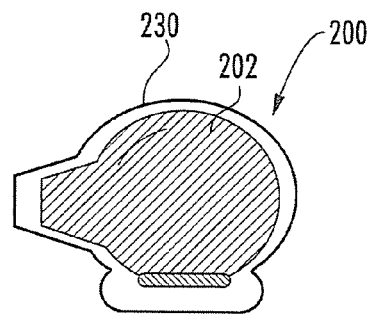
FIG. 10C is cross-sectional view of an earbud module for the headset of FIG. 10A with a cover, according to some embodiments of the present invention.

Referring to FIGS. 10A-10C, a monitoring apparatus, according to other embodiments of the present invention, is illustrated. The illustrated monitoring apparatus is a headset 300 with an earbud module 200 and an ear hook 105 for securing the headset 300 to the ear of a user. Different sizes and shapes of ears may require different earbud sizes and shapes. For this reason, a detachable cover 230 is removably secured to the earbud module housing 202, as shown in FIGS. 10B-10C. Detachable covers of various sizes may be provided, according to embodiments of the present invention. As such an earbud module may be custom fit to a particular ear of a user by selecting a cover 230 having a shape that best matches the shape of a user ear.

Figure 12:
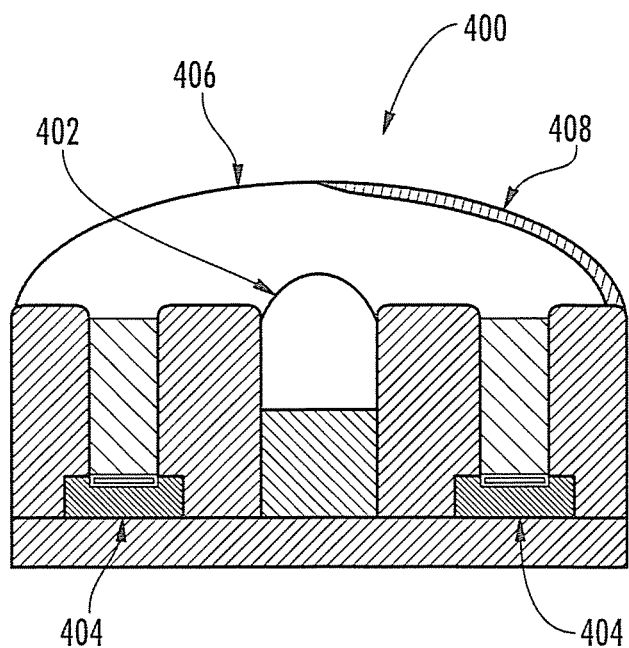
FIG. 12 is a cross-sectional view of an optical sensor module, according to some embodiments of the present invention.

Referring now to FIG. 12, an optical sensor module 400 that may be incorporated into a sensor region 204 of a monitoring apparatus, according to embodiments of the present invention, is illustrated. The illustrated optical sensor module 400 includes at least one optical emitter 402 and a plurality of optical detectors 404. Covering the optical emitter 402 and detectors 404 is at least one lens 406. The lens 406 includes an optical regulating region 408 that prevents at least one region of the optical sensor module 400 from receiving light scattered by physiological material. The optical regulating region 408 may be located at any region that prevents optical energy having physiological information from reaching at least one detector 404. In the illustrated embodiment, the optical regulating region 408 is at least partially reflective of light.

In other embodiments, the optical sensor module 400 may include more than one optical emitter 402 and at least one optical detector 404 to generate equal results, as long as the optical energy from the at least one optical emitter 402 is regulated by at least one energy regulating region 408. In some embodiments, the optical emitter 402 and detectors 404 may be isolated by an optical blocking material to prevent unwanted optical signals from triggering the optical detectors.

Referring to FIGS. 11A-11B, a monitoring apparatus 200 in the form of an earbud module includes a housing 202 that is configured to be attached to the ear E of a subject. The housing 202 includes multiple sensor regions 204, 204', 204" that are configured to contact respective selected areas of an ear E when the housing 202 is attached to the ear E. Each sensor region 204, 204', 204" is contoured to matingly engage a respective selected ear area. At least one physiological sensor and/or environmental sensor is associated with each sensor region that is configured to detect and/or measure physiological and/or environmental information from the subject. The use of multiple sensor regions 204, 204', 204" facilitates the extraction of motion artifacts from physiological sensor readings. In the illustrated embodiment, sensor region 204 includes sensors for detecting physiological and/or environmental information. Sensor regions 204' and/or 204" may be associated with sensors for detecting motion. For example, in some embodiments, signals detected at the motion sensor regions 204' may be used to detect speech to facilitate noise cancellation and/or sensor regions 204" may be used to detect generalized motion of the human body, such as motion during writing, clapping, walking, jogging, running, or the like. This description of sensor regions is not meant to limit the invention. A variety of spatial sensor configurations may be used to extract physiological information and reduce noise.

Figure 13A:
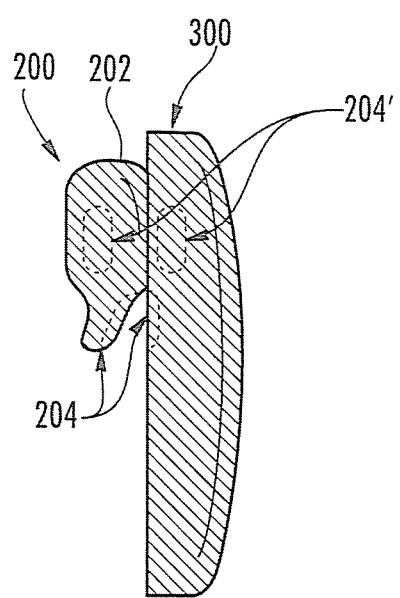
FIG. 13A is a side view of a headset having an earbud module, according to some embodiments of the present invention.
Figure 13B:
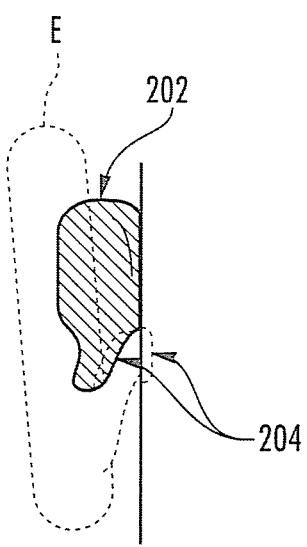
FIG. 13B illustrates the headset of FIG. 13A attached to an ear of a subject.

Monitoring apparatus, according to embodiments of the present invention, may include sensor regions associated with reflection-mode sensors and/or sensor regions associated with transmission-mode sensors. The term "reflection-mode" refers to a method of measuring physiological information with scattered excitation energy that has not fully penetrated a part of the body of a subject. The term "transmission-mode" refers to a method of measuring physiological information with scattered excitation energy that has fully penetrated at least one part of the body of a subject. FIGS. 13A-13B illustrate a transmission-mode earbud module 200. The earbud module 200 is attached to a headset 300. A pair of sensor regions 204 are in adjacent, spaced-apart relationship, as illustrated, with one sensor region 204 on the earbud module 200 and the other sensor region 204 on the headset 300. These sensor regions 204 are configured to pass energy from one to the other when the tragus region of an ear E of a subject is positioned between these sensor regions. In the illustrated embodiment, the earbud module 200 and headset 300 also include sensor regions 204' in adjacent, spaced-apart relationship. In this configuration, the anti tragus can be positioned between the two sensor regions 204' for emitting and detecting energy.

Figure 14A:
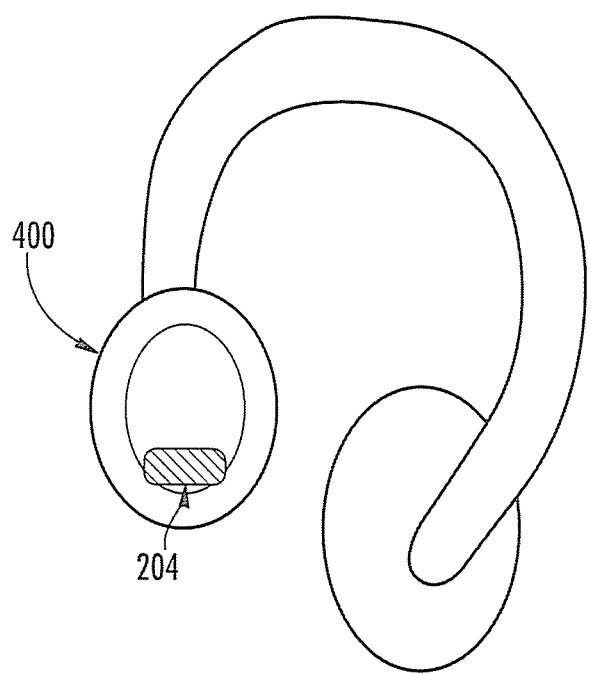
FIG. 14A is a perspective view of a headset with earmuffs and wherein an earmuff thereof includes a sensor region, according to some embodiments of the present invention.
Figure 14B:
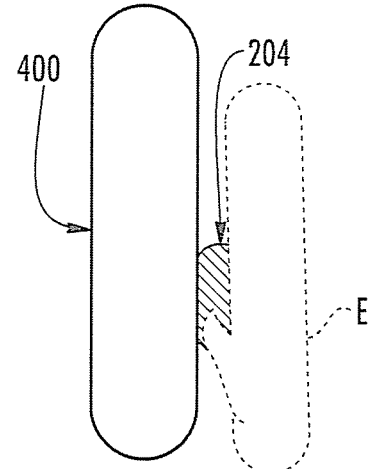
FIG. 14B illustrates the headset of FIG. 14A attached to an ear of a subject.

Embodiments of the present invention may be utilized in form-factors other than traditional earbud designs. FIGS. 14A-14B illustrate a sensor region in an earmuff 400, where the sensor region 204 is part of the earmuff form-factor. The sensor region 204 is located in the earmuff 400 such that the sensor region 204 is in proximity to at least one region of the ear E of a subject.

Health and environmental monitors, according to embodiments of the present invention, enable low-cost, real-time personal health and environmental exposure assessment monitoring of various health factors. An individual's health and environmental exposure record can be provided throughout the day, week, month, or the like. Moreover, because the health and environmental sensors can be small and compact, the overall size of an apparatus, such as an earpiece, can remain lightweight and compact.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A monitoring apparatus, comprising:
an earbud module configured to be attached to an ear of a subject, the ear having an anti tragus, an acoustic meatus, and an ear canal, wherein the earbud module comprises a sensor region having at least one optical sensor that is configured to detect and/or measure physiological information from the subject, wherein the sensor region is contoured to matingly engage at least one portion of the intersection of the anti tragus and acoustic meatus, and wherein the sensor region is oriented in a direction away from the ear canal.

2. The apparatus of claim 1, wherein the sensor region contour stabilizes the earbud module when the earbud module is attached to the ear of the subject.

3. The apparatus of claim 1, further comprising at least one environmental sensor associated with the sensor region that is configured to detect and/or measure environmental information.

4. The apparatus of claim 1, wherein at least a portion of the sensor region is removable and replaceable with another sensor region having a different contour.

5. The apparatus of claim 1, wherein the apparatus is a headset and wherein the sensor region is a portion of an earbud housing of the headset.

6. The apparatus of claim 1, wherein the at least one optical sensor comprises a plurality of optical sensors.

7. The apparatus of claim 3, wherein the at least one environmental sensor comprises a plurality of environmental sensors.

8. The apparatus of claim 1, wherein the at least one optical sensor comprises:
at least one optical emitter;
a plurality of optical detectors; and
a lens that covers the at least one optical emitter and the plurality of optical detectors, wherein the lens comprises a region that prevents light containing physiological information from reaching at least one of the detectors.

9. The apparatus of claim 8, wherein at least one portion of the lens is configured to guide light transferred from the subject to at least one of the optical detectors.

10. The apparatus of claim 8, wherein the lens is configured to focus light transferred from the subject to at least one of the optical detectors.

11. The apparatus of claim 1, wherein the earbud module comprises an elongated hollow tube extending outwardly therefrom that is configured to be inserted within an ear canal of the subject.

12. The apparatus of claim 11, wherein the elongated hollow tube comprises a sensor region having one or more motion sensors associated therewith that are configured to measure motion of the subject, wherein the one or more motion sensors are configured to measure changes in one or more of the following: inertia, capacitance, electrical conductivity, inductance, speed, distance, acceleration, and electromagnetic radiation.

13. The apparatus of claim 1, further comprising a cover detachably secured to the sensor region.

14. The apparatus of claim 13, wherein at least one portion of the cover is configured to regulate energy transferred from the subject to the at least one optical sensor.

15. The apparatus of claim 13, wherein at least one portion of the cover is configured to block energy transferred from the subject to the at least one optical sensor.

16. The apparatus of claim 1, wherein the sensor region comprises one or more motion sensors configured to measure motion of the subject, and wherein the one or more motion sensors configured to measure motion are configured to measure changes in one or more of the following: inertia, capacitance, electrical conductivity, inductance, speed, distance, acceleration, and electromagnetic radiation.

17. The apparatus of claim 8, wherein the lens region comprises a portion that vibrates in response to body motion of the subject and modulates light passing through the lens region in proportion to the body motion of the subject.

18. The apparatus of claim 15, wherein the at least one optical sensor comprises:
at least one optical emitter; and
a plurality of optical detectors, wherein at least a portion of the cover is configured to block light from reaching at least one of the optical detectors.

19. The apparatus of claim 18, wherein the cover comprises a portion that vibrates in response to body motion of the subject and modulates light passing through the cover in proportion to the body motion of the subject.

20. A monitoring apparatus, comprising:
an earbud module configured to be attached to an ear of a subject, the ear having an anti tragus, an acoustic meatus, and an ear canal, wherein the earbud module comprises a sensor region having at least one optical sensor that is configured to detect and/or measure physiological information from the subject, wherein the sensor region is contoured to matingly engage at least one portion of the intersection of the anti tragus and acoustic meatus, wherein the sensor region is oriented in a direction away from the ear canal, and wherein the sensor region is removably secured to the earbud module via a connector, wherein the connector facilitates ready removal from and attachment to the earbud module.

21. The apparatus of claim 20, wherein the sensor region contour stabilizes the earbud module when the earbud module is attached to the ear of the subject.

22. The apparatus of claim 20, further comprising at least one environmental sensor associated with the sensor region that is configured to detect and/or measure environmental information.

23. The apparatus of claim 20, wherein the apparatus is a headset and wherein the sensor region is a portion of an earbud housing of the headset.

24. The apparatus of claim 20, wherein the at least one optical sensor comprises a plurality of optical sensors.

25. The apparatus of claim 22, wherein the at least one environmental sensor comprises further comprising a plurality of environmental sensors.

26. The apparatus of claim 20, wherein the at least one optical sensor comprises:
at least one optical emitter;
a plurality of optical detectors; and
a lens that covers the at least one optical emitter and the plurality of optical detectors, wherein the lens comprises a region that prevents light containing physiological information from reaching at least one of the detectors.

27. The apparatus of claim 26, wherein at least one portion of the lens is configured to guide light transferred from the subject to at least one of the optical detectors.

28. The apparatus of claim 26, wherein the sensor region comprises a portion that vibrates in response to body motion of the subject and modulates light passing through the sensor region in proportion to the body motion.

29. The apparatus of claim 20, wherein at least one portion of the sensor region overlies at least a portion of the at least one optical sensor and is configured to guide energy transferred from the subject to the at least one optical sensor.

30. The apparatus of claim 20, wherein the sensor region comprises a lens configured to focus light transferred from the subject to the at least one optical sensor.

31. The apparatus of claim 20, wherein the earbud module comprises a plurality of sensor regions, each configured to contact a respective selected area of the ear of the subject when the earbud module is attached to the ear of the subject, each contoured to matingly engage a respective selected ear area, and further comprising at least one optical sensor associated with each sensor region that is configured to detect and/or measure physiological information from the subject.

32. The apparatus of claim 20, wherein the earbud module comprises a plurality of sensor regions, each configured to contact a respective selected area of the ear of the subject when the earbud module is attached to the ear of the subject, each contoured to matingly engage a respective selected ear area, wherein at least one sensor region has one or more sensors associated therewith that are configured to measure motion of the subject, and wherein at least one sensor region has one or more sensors associated therewith that are configured to measure physiological information from the subject.

33. The apparatus of claim 32, wherein the one or more sensors configured to measure motion of the subject are configured to measure changes in one or more of the following: inertia, capacitance, electrical conductivity, inductance, speed, distance, acceleration, and electromagnetic radiation.

34. The apparatus of claim 20, further comprising a cover detachably secured to the sensor region.

35. The apparatus of claim 34, wherein at least one portion of the cover is configured to regulate energy transferred from the subject to the at least one optical sensor.

36. The apparatus of claim 34, wherein at least one portion of the cover is configured to block energy transferred from the subject to the at least one optical sensor.

37. The apparatus of claim 36, wherein the at least one portion of the cover is configured to block light from passing therethrough.

38. The apparatus of claim 36, wherein the cover comprises a portion that vibrates in response to body motion of the subject and modulates light passing through the sensor region in proportion to the body motion.

39. A monitoring apparatus, comprising:
an earbud module configured to be attached to an ear of a subject, the ear having an anti tragus, an acoustic meatus, and an ear canal, wherein the earbud module comprises a sensor region having at least one electromagnetic emitter and at least one electromagnetic sensor, wherein the sensor region emits electromagnetic energy to at least one portion of the intersection of the anti-tragus and acoustic meatus in a direction away from the ear canal and/or detects electromagnetic energy from at least one portion of the intersection of the anti-tragus and acoustic meatus in a direction away from the ear canal, and wherein the at least one electromagnetic sensor comprises one or more of the following: an optical sensor, a capacitive sensor, an acoustic sensor, an auscultatory sensor, a pressure sensor, or a color sensor.

40. The apparatus of claim 39, further comprising at least one environmental sensor associated with the sensor region that is configured to detect and/or measure environmental information.

41. The apparatus of claim 39, wherein the apparatus is a headset and wherein the sensor region is a portion of an earbud housing of the headset.

42. The apparatus of claim 39, wherein the at least one electromagnetic sensor comprises a plurality of electromagnetic sensors.

43. The apparatus of claim 40, wherein the at least one environmental sensor comprises a plurality of environmental sensors.

44. The apparatus of claim 39, wherein the sensor region comprises one or more motion sensors configured to measure motion of the subject, and wherein the one or more motion sensors configured to measure motion are configured to measure changes in one or more of the following: inertia, capacitance, electrical conductivity, inductance, speed, distance, acceleration, and electromagnetic radiation.

45. The apparatus of claim 1, wherein the earbud module comprises a plurality of sensor regions, each configured to contact a respective selected area of the ear of the subject when the earbud module is attached to the ear of the subject, each contoured to matingly engage a respective selected ear area, and further comprising at least one optical sensor associated with each sensor region that is configured to detect and/or measure physiological information from the subject.

* * * * *

UNITED STATES PATENT AND TRADEMARK OFFICE
CERTIFICATE OF CORRECTION

PATENT NO. : 8,647,270 B2  
APPLICATION NO. : 12/692807  
DATED : February 11, 2014  
INVENTOR(S) : LeBoeuf et al.

Page 1 of 1

It is certified that error appears in the above-identified patent and that said Letters Patent is hereby corrected as shown below:

In the Specification:
Column 4, Line 14: Please correct "FIG. 50 is a front"
to read -- FIG. 5C is a front --

Signed and Sealed this
Twenty-third Day of September, 2014

Michelle K. Lee
*Deputy Director of the United States Patent and Trademark Office*